United States Patent [19]
Meyerrose

[11] Patent Number: 6,115,849
[45] Date of Patent: *Sep. 12, 2000

[54] ADJUSTABLE STRAP FOR SCUBA MASK

[76] Inventor: Kurt E. Meyerrose, P.O. Box 490, Alstead, N.H. 03602

[ * ] Notice: This patent is subject to a terminal disclaimer.

[21] Appl. No.: 09/399,877

[22] Filed: Sep. 20, 1999

Related U.S. Application Data

[62] Division of application No. 09/014,231, Jan. 27, 1998.

[51] Int. Cl.⁷ ..................................................... A61F 9/02
[52] U.S. Cl. ..................................................... 2/452; 2/428
[58] Field of Search ............................ 2/452, 428, 430, 2/426, 9, 338; 128/207.11, 207.17, 201.22; 351/43

[56] References Cited

U.S. PATENT DOCUMENTS

| | | |
|---|---|---|
| D. 324,589 | 3/1992 | Dagnino . |
| D. 343,029 | 1/1994 | Berenson ................. D16/311 |
| D. 361,081 | 8/1995 | Pardinas .................. D16/339 |
| D. 388,452 | 12/1997 | Dreyfus . |
| 2,312,630 | 3/1943 | Dauster ................. 128/207.11 |
| 3,606,648 | 9/1971 | Schuler ................... 24/16 PB |
| 4,112,521 | 9/1978 | Uke ............................. 2/452 |
| 4,562,836 | 1/1986 | Perron ................... 128/201.11 |
| 4,657,364 | 4/1987 | Murrell ..................... 351/156 |
| 4,692,002 | 9/1987 | Meistrell ................... 351/156 |
| 4,743,105 | 5/1988 | Tabacchi ................... 351/156 |
| 4,820,036 | 4/1989 | Seet ........................ 351/156 |
| 4,910,806 | 3/1990 | Baker et al. ................. 2/452 |
| 5,046,200 | 9/1991 | Feder ......................... 2/452 |
| 5,357,654 | 10/1994 | Hsing-Chi .............. 24/68 B |
| 5,555,571 | 9/1996 | McCaffrey .................. 2/428 |
| 5,878,443 | 3/1999 | Seller ........................ 2/426 |

*Primary Examiner*—Peter Nerbun
*Attorney, Agent, or Firm*—Davis and Bujold

[57] ABSTRACT

A scuba mask which can be easily and quickly repositioned when the diver descends into deep water, wherein the pressure change causes the scuba mask to become loose. The coupling member between the fabric body portion and the adjustable straps is flared, increasing its surface area, and allowing any tension created within the scuba mask strap, during use, to be equally distributed throughout the mask.

20 Claims, 3 Drawing Sheets

ADJUSTABLE STRAP FOR SCUBA MASK

This application is a divisional of Ser. No. 09/014,231 filed Jan. 27, 1998.

FIELD OF THE INVENTION

In the past, completely rubber-type mask straps were used to secure the scuba mask to the head of the diver. These straps have since been replaced with fabric-laminated, soft headbands. These straps allow for an increase in ease of comfort and avoid tangling of the diver's hair in the strap. The disadvantage of the soft headbands is that they do not hold their position on the back of the diver's head as well as the rubber-type mask straps.

While the tangling of hair is of concern to the diver, the use of a fabric to contact the head allows for slippage. The rubber-type masks of the past have a higher coefficient of friction thereby allowing for secure placement, although comfort is compromised. In addition, the fabric-laminated strap is at a disadvantage in that if the diver is wearing a hood, even more slippage is possible.

The Feder mask strap, in U.S. Pat. No. 5,046,200, avoids the problem incurred by the rubber-type masks by using a soft hook-type fastening material. However, this material is a disadvantage in that it has a tendency to wear out quickly thereby making for a weaker connection. In addition, the mask can not be quickly repositioned while under water which is a safety concern.

When a diver descends into deeper water, the pressure surrounding the diver increases. This causes the fabric-laminated straps, which are usually made of material such as neoprene or foam, to expand thus creating slippage or leakage around the diver's mask. A strap that can be easily and quickly repositioned, e.g. tightened, would be advantageous under these conditions.

SUMMARY OF THE INVENTION

Wherefore, it is an object of the present invention to overcome the aforementioned problems and drawbacks associated with the prior art designs.

The present invention relates to a device used in scuba diving and the method used in its production. The device allows for an increase in comfort provided to the diver during use. In addition, it is easily adjustable under water which increases both the level of safety and stability.

In one embodiment, the scuba mask strap is comprised of a fabric body portion and a means for fastening the body portion to a scuba mask. The means for fastening comprising at least two adjustable straps located on opposing sides of the body portion. Each adjustable strap has a coupling member, on a proximal end, that attaches the body portion to the adjustable strap, and an opposed tapered end to allow for easy threading of the adjustable strap through one of the elongated slots located on either side of the scuba mask. The body portion is then stitched to the coupling member of the adjustable strap to secure it. The body portion is constructed of a neoprene material, which is both flexible and strong as well as having a certain degree of elasticity. The coupling member is composed of a rigid plastic portion encased within an elastomer portion. The rigid plastic portion has an elongated slot to allow one end of a fabric coupling member to loop through the slot and be folded back onto itself and secured to the body portion. The adjustable strap is about 8–10 inches in length, with a plurality of raised ridges along its surface. The ridges are spaced about one centimeter apart along the entire length of the adjustable strap.

The present invention relates to a scuba mask strap comprising: an elongate fabric body portion having a wider central area and opposed first and second narrower sections; and a pair of resilient adjustable straps members which each have a flared section, located adjacent one end thereof, and said flared section of each said adjustable strap members being securely fastened to one of the first and second narrower sections of said body portion.

The present invention also relates to a resilient adjustable strap member for use in manufacturing a scuba mask strap, said adjustable strap member comprising an elongate member having a flared section, located adjacent one end thereof, and an opposed tapered end, said flared section supporting a coupling member, said coupling member comprising an elongate, flared body portion which is integrally formed with a thickened body portion, and an elongate slot is provided in said coupling member for coupling said adjustable strap member to a body portion, and a first surface of said adjustable strap member being provided with a plurality of equally spaced apart ribs.

The present invention finally relates to a method of manufacturing a scuba mask strap, said method comprising the steps of: providing an elongate fabric portion with a wider central area and opposed first and second narrower sections; providing a pair of resilient adjustable strap members each having a tapered first end, to facilitate attachment of the adjustable strap member to a desired scuba mask, and an opposed second end with a flared section; and permanently securing said flared second end of each of said adjustable strap members to one of said of first and second narrower sections of said fabric body to form said scuba mask strap.

The device, as described, is not to be limited to only the above description, but is further explained in the accompanying figures.

BRIEF DESCRIPTION OF THE DRAWINGS

The invention will now be described, by way of example, with reference to the accompanying drawings in which.

DESCRIPTION OF THE PREFERRED EMBODIMENTS

The present invention is particularly directed at providing a scuba mask strap which is manufactured from two materials having different characteristics, e.g. a fabric body portion and a pair of opposed resilient or rubber adjustable strap members. More particularly, the present invention is directed at providing a secured attachment of the two opposed adjustable strap members to the body portion.

Figure 1:
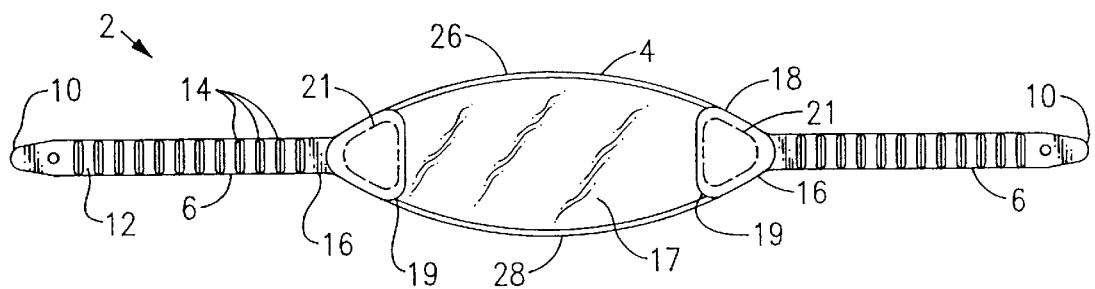
FIG. 1 is a diagram illustration of a first embodiment of a scuba mask strap according to the present invention.

Turning now to FIG. 1, a detailed description concerning a first embodiment of the present invention will now be provided. As can be seen in that figure, the scuba mask strap 2 comprises a body portion 4 and a pair of opposed adjustable strap members 6. The body portion 4 typically is manufactured from neoprene or some other light weight fabric material while the adjustable strap members 6 are ordinarily manufactured from a rubber or other conventional resilient material which is typically used to manufacture conventional scuba mask straps.

Each one of the adjustable strap members 6 has a first tapered end 10 to facilitate insertion of that end of the adjustable strap member 6 into a conventional coupling of a suitable scuba mask (not shown). In addition, a first surface 12 of the adjustable strap member 6 is provided with a plurality of equally spaced apart ribs 14, e.g. the ribs are approximately 0.5 cm wide, about 0.29 cm high and spaced approximately 1 cm apart. As such ribs are well known in the art, a further detailed description concerning the same is not provided. The opposed surface 13 of the strap member 6 is flat.

The opposite second end 16 of the adjustable strap member 6 has a flared section 18 to provide an increased surface area for facilitating attachment of the second end 16 of the adjustable strap member 6 to the body portion 4. The body portion 4 is typically an oval shaped member which has a wider width in the central area 17 of the body portion 4 and tapers at each opposed end of the body portion 4 to a narrower section 19. Each one of the flared sections 18 (FIGS. 1–3) of the adjustable strap members 6 is secured to one of the two narrower sections 19 of the body portion 4.

Due to the increase surface area of the flared section 18 of the second end of the adjustable strap member 6, secure attachment to the two narrower sections 19 of the body portion 4 can be obtained. Such attachment is achieved by sufficiently overlapping the flared section 18 of one of the adjustable strap members 6 over the narrower section 19 of the body portion 4 and stitching 21 around the perimeter of flared section 18 to provide a secure connection between those two components. The other adjustable strap member 6 is similarly attached to the opposite narrower section 19 of the body portion 4. Such connection between the adjustable strap members 6 and the body portion 4 allows any tension created within the scuba mask strap, during use, to be equally distributed between those three interconnected components. In addition, due to the oval shape of the body portion 4, when the body portion 4 is under tension, it has a tendency to "cup" into a C-shaped configuration as the two opposed longitudinal edge surfaces 26, 28 of the body portion 4 are tensioned. This tension facilitates adaptation of the body portion 4 to the contour of the back of a head of a user and renders the scuba mask strap, according to the present invention, more comfortable to wear.

Figure 2:
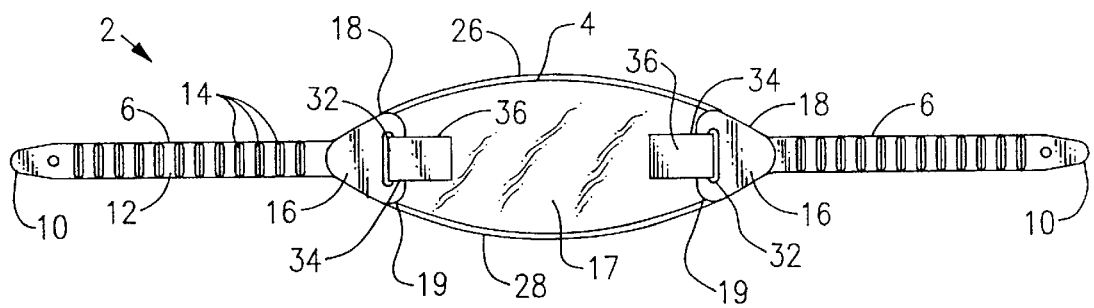
FIG. 2 is a diagram illustration of a second embodiment of a scuba mask strap according to the present invention.

Turning now to FIG. 2, an alternative attachment of the adjustable straps members 6 to the body portion 4 is shown. In this embodiment, each flared section 18 of the adjustable strap member 6 is provided with an aperture 32 and a continuous loop 34 is passed through the aperture 32 and is sewn, stitched or otherwise permanently fastened 36 to the body portion 4. In all other respects, this embodiment is substantially identical to the previously described embodiment.

Figure 3:
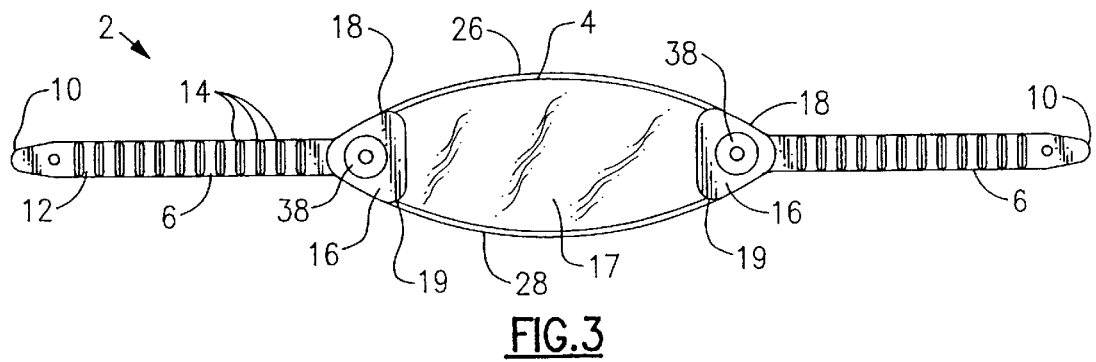
FIG. 3 is a diagram illustration of a third embodiment of a scuba mask strap according to the present invention.
Figure 4:
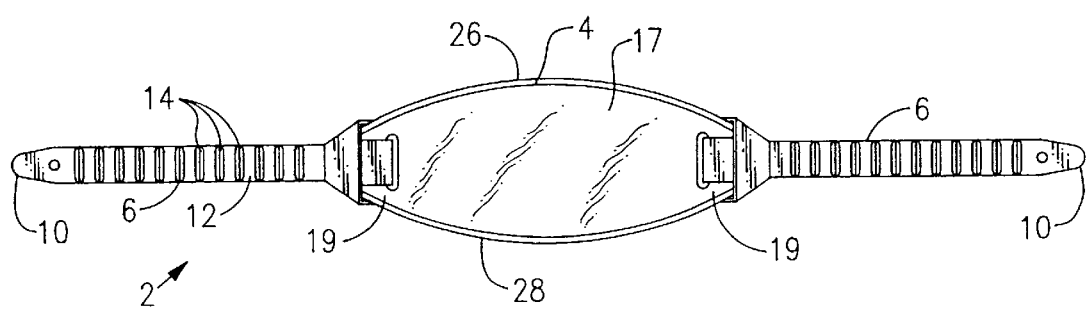
FIG. 4 is a diagram illustration of a fourth embodiment of a scuba mask strap according to the present invention.
Figure 5:
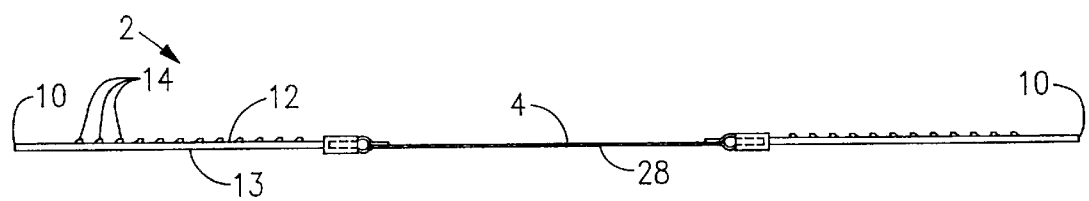
FIG. 5 is a side elevation view of the scuba mask strap of FIG. 4.
Figure 6:
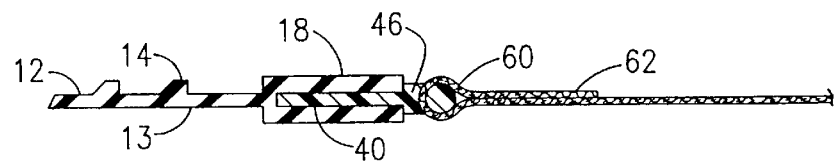
FIG. 6 is a cross-sectional view of the scuba mask strap of FIG. 4 along section 6—6 line.
Figure 7:
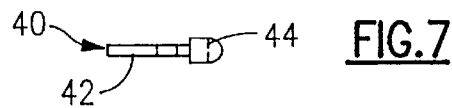
FIG. 7 is a side view of the molded coupling member of FIG. 4.
Figure 8:
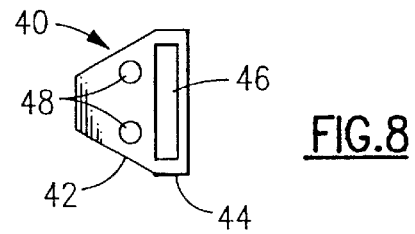
FIG. 8 is a top plan view of the coupling member of FIG. 7.

With reference to FIG. 3, a third embodiment of the present invention can be seen. This embodiment is also substantially identical to the first embodiment except that a rivet 38, e.g. a plastic or metal rivet, extends completely through a central area of the flared section 18 of the adjustable strap member 6 and the narrower section 19 of the body portion 4 to secure those two components to one another. The opposed ends of the rivet are sufficiently wide to permanently maintain the connection between the flared section 18 and the narrower section 19.

With reference to FIGS. 4–12, a fourth and preferred embodiment of the present invention will now be described. This embodiment, like the previous three embodiments, also comprises a body portion 4 which supports a pair of opposed adjustable strap members 6. The difference between this embodiment and the previous embodiments is that the flared sections 18 of the adjustable strap members 6 permanently support an intermediate coupling member 40 (see FIGS. 7 and 8). The coupling member 40 comprises an elongate, flared body portion 42 which is integrally formed with a thickened body portion 44. An elongate slot 46 is provided in the coupling member 40 at or adjacent a transition between the flared body portion 42 and the thickened body portion 44. In addition, a central region of the flared body portion 42 is provided with a pair of through holes 48 which facilitate permanent attachment of the coupling member 40 to the flared section 18 of the adjustable strap member 6. This permanent attachment is conventionally achieved during manufacture of the adjustable strap member 6. That is, the coupling member 40 is initially molded first and then is provided in a conventional mold for molding the adjustable strap member 6. As the adjustable strap member 6 is manufactured, the coupling member 40 is securely and integrally fastened, by the molding process, with the adjustable strap member 6. That is, the moldable rubber-like material flows through the two through holes 48 and about the exterior surface of the coupling member 40 to form the secure attachment therebetween. This molded arrangement can be seen in FIGS. 11 and 12.

Figure 9:
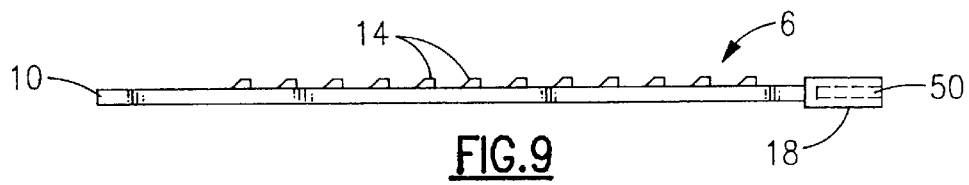
FIG. 9 is a side view of the rubber strap without the molded coupling member.
Figure 10:
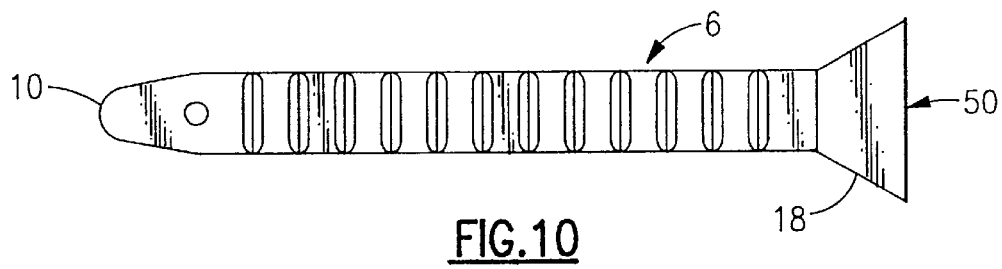
FIG. 10 is a top plan view of the rubber strap of FIG. 9.
Figure 11:
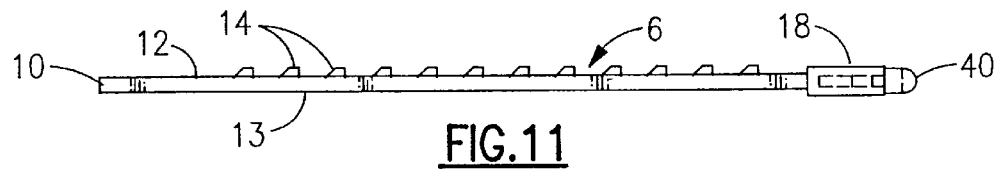
FIG. 11 is a side view of the rubber strap and coupling member formed as a complete unit.
Figure 12:
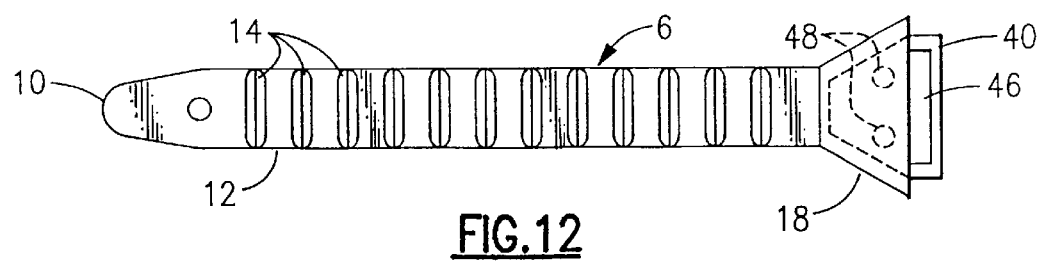
FIG. 12 is a top plan view of the complete unit of FIG. 11.

FIGS. 9 and 10 show a side elevational and a top plan view, respectively, of the adjustable strap 6 being molded without the coupling member 40 secured thereto. According to this variation of the invention, the flared section 18 of the adjustable strap 6 is provided with a recess or cavity 50 which is sized to intimately and closely receive the flared body portion 42 of the coupling member 40. The coupling member 40 can thereafter be glued, riveted or otherwise permanently fastened with the cavity 50 so that the coupling member 40 is permanently retained by the adjustable strap member 6.

A fabric coupling member 60 is passed through the elongate slot 46 (FIGS. 4–6) of one of the coupling members 40 and the two opposed ends of the fabric coupling member 60 are stitched or otherwise permanently secured 62 to one of the narrower sections 19 of the body portion 4. The other adjustable strap member 6 is similarly attached to the other narrower section 19 of the body portion 4.

Since certain changes may be made in the above described scuba mask strap, without departing from the spirit and scope of the invention herein involved, it is intended that all of the subject matter of the above description or shown in the accompanying drawings shall be interpreted merely as examples illustrating the inventive concept herein and shall not be construed as limiting the invention.

Wherefore I/we claim:

1. A scuba mask strap comprising:
    an elongate head portion, for supporting a mask at a head of a user, having a relatively wide central area and opposed first and second narrower sections;
    a pair of resilient adjustable strap members each having a flared section located adjacent a proximal end thereof, and each of the flared sections of the adjustable strap members being securely fastened to one of the first and second narrower sections of the head portion by a respective coupling member.

2. The scuba mask strap according to claim 1, wherein the head portion is an oval shaped member.

3. The scuba mask strap according to claim 1, wherein the head portion is manufactured from neoprene.

4. The scuba mask strap according to claim 1, wherein an opposite end of each of the pair of adjustable strap members is tapered to facilitate insertion of the tapered end of each of the pair of adjustable strap members into a conventional coupling of a desired scuba mask.

5. The scuba mask strap according to claim 1, wherein a first surface of each of the pair of adjustable strap members is provided with a plurality of equally spaced apart ribs.

6. The scuba mask strap according to claim 5, wherein each of the plurality of equally spaced apart ribs is approximately 0.29 centimeters high, approximately 0.5 centimeters wide and spaced approximately 1 centimeter apart from adjacent equally spaced apart ribs.

7. The scuba mask strap according to claim 1, wherein a second opposed surface of each of the pair of adjustable strap members is flat.

8. The scuba mask strap according to claim 1, wherein each of the pair of adjustable strap members has an axial length of about 8 to about 10 inches.

9. The scuba mask strap according to claim 1, wherein the coupling member is a loop, a central region of the flared body portion is provided with an aperture through which the loop is passed to secure the adjustable strap member to the one of the first and second narrower sections of the elongate head portion.

10. The scuba mask strap according to claim 9, wherein the loop is a fabric member which passes through the aperture and opposed ends of the fabric member are permanently secured to one of the first and second narrower sections of the head portion.

11. The scuba mask strap according to claim 2, wherein the flared section of each pair of resilient adjustable strap members provides an increased surface area for facilitating attachment of the proximal end of the adjustable strap member to one of the first and second narrower sections of the head portion.

12. The scuba mask strap according to claim 2, wherein each flared section, of said pair of resilient adjustable strap members, sufficiently overlapping one of the first and second narrower sections of the head portion and a perimeter portion of the flared section of a first one of the pair of resilient adjustable strap members is stitched to the first narrower section of the head portion to provide a secure connection therebetween and a perimeter portion of the flared section of a second one of the pair of resilient adjustable strap members is stitched to the second narrower section of the head portion to provide a secure connection therebetween.

13. The scuba mask strap according to claim 2, wherein the head portion allows any tension created within the scuba mask strap to be equally distributed, during use, between the elongate head portion and the pair of resilient adjustable strap members.

14. The scuba mask strap according to claim 2, wherein when the body portion is under tension, the body portion has a tendency to cup into a C-shaped configuration as two opposed longitudinal edge surfaces of the body portion are tensioned, and this C-shaped configuration adapts the body portion to the contour of a back of a head of a user.

15. The scuba mask strap according to claim 2, wherein each flared section, of said pair of resilient adjustable strap members, sufficiently overlapping one of the first and second narrower sections of the head portion and a rivet secures the flared section of a first one of the pair of resilient adjustable strap members to the first narrower section of the head portion and a rivet secures the flared section of a second one of the pair of resilient adjustable strap members to the second narrower section of the head portion.

16. The scuba mask strap according to claim 15, wherein the rivet is one of a plastic and a metal rivet extending completely through a central area of the flared section and through one of the first and second narrower sections of the head portion to permanently secure those two components to one another.

17. The scuba mask strap according to claim 2, wherein the flared section of each pair of resilient adjustable strap members provides an increased surface area for facilitating attachment of the proximal end of the adjustable strap member to one of the first and second narrower sections of the head portion; and
    the head portion allows any tension created within the scuba mask strap to be equally distributed, during use, between the elongate head portion and the pair of resilient adjustable strap members.

18. The scuba mask strap according to claim 17, wherein when the head portion is under tension, the portion has a tendency to cup into a C-shaped configuration as two opposed longitudinal edge surfaces of the body portion are tensioned, and this C-shaped configuration adapts the head portion to the contour of a back of a head of a user.

19. The scuba mask strap according to claim 2, wherein an opposite end of each of the pair of adjustable strap members is tapered to facilitate insertion of the tapered end of each of the pair of adjustable strap members into a conventional coupling of a desired scuba mask;
    a first surface of each of the pair of adjustable strap members is provided with a plurality of equally spaced apart ribs;
    a second opposed surface of each of the pair of adjustable strap members is flat; and
    each of the pair of adjustable strap members has a length of about 8 to about 10 inches.

20. A resilient adjustable scuba mask strap comprising:
    an elongate head portion having a relatively wide central area and opposed first and second narrower sections:
    an elongate adjustable first strap member having a flared section, located adjacent a proximal end thereof, and a tapered end, located adjacent a distal opposed end thereof; the flared section of the adjustable first strap member supporting a coupling member for coupling the adjustable first strap member to the first narrower section of the head portion, and a first surface of the adjustable first strap member being provided with a plurality of equally spaced apart ribs; and
    an elongate adjustable second strap member having a flared section, located adjacent a proximal end thereof, and a tapered end, located adjacent a distal oppose end thereof; the flared section of the adjustable second strap member supporting a coupling member for coupling the adjustable second strap member to the second narrower section of the head portion, and a first surface of the adjustable second strap member being provided with a plurality of equally spaced apart ribs.

* * * * *